(12) United States Patent
Willis et al.

(10) Patent No.: US 9,107,833 B2
(45) Date of Patent: Aug. 18, 2015

(54) REHYDRATABLE PHARMACEUTICAL PRODUCT

(75) Inventors: Sean Willis, Surrey (GB); Rosemary Palmer, Surrey (GB)

(73) Assignee: BIOCOMPATIBLES UK LIMITED, Farnham Surrey (GB)

( * ) Notice: Subject to any disclaimer, the term of this patent is extended or adjusted under 35 U.S.C. 154(b) by 1351 days.

(21) Appl. No.: 12/305,048

(22) PCT Filed: Jun. 22, 2007

(86) PCT No.: PCT/EP2007/056282
§ 371 (c)(1),
(2), (4) Date: Jan. 8, 2009

(87) PCT Pub. No.: WO2007/147902
PCT Pub. Date: Dec. 27, 2007

(65) Prior Publication Data
US 2009/0274762 A1    Nov. 5, 2009

(30) Foreign Application Priority Data

Jun. 22, 2006  (EP) .................................... 06253242

(51) Int. Cl.
| | |
|---|---|
| *A61K 9/00* | (2006.01) |
| *A61K 9/16* | (2006.01) |
| *B82Y 5/00* | (2011.01) |
| *A61K 9/19* | (2006.01) |

(52) U.S. Cl.
CPC ................. *A61K 9/19* (2013.01); *A61K 9/0019* (2013.01); *A61K 9/1676* (2013.01); *B82Y 5/00* (2013.01)

(58) Field of Classification Search
CPC ..... A61K 9/19; A61K 9/0019; A61K 9/1676; B82Y 5/00
See application file for complete search history.

(56) References Cited

U.S. PATENT DOCUMENTS

| | | | |
|---|---|---|---|
| 5,393,527 A  * | 2/1995 | Malick et al. ................. 435/7.1 |
| 6,564,471 B1 * | 5/2003 | Sutherland et al. ............. 34/284 |
| 2005/0002934 A1* | 1/2005 | Reed .......................... 424/145.1 |
| 2006/0034923 A1* | 2/2006 | Li et al. ......................... 424/468 |

FOREIGN PATENT DOCUMENTS

| | | |
|---|---|---|
| WO | 99/12577 A1 | 3/1999 |
| WO | 2004/060059 A2 | 7/2004 |
| WO | 2004/071495 A1 | 8/2004 |
| WO | 2005/087193 A2 | 9/2005 |
| WO | 2006/027567 A2 | 3/2006 |

OTHER PUBLICATIONS

Y. Machida et al., "Pharmacokinetics of prolonged-release CPT—11-loaded microspheres in rats", Journal of Controlled Release, Elsevier Science Publishers B.V., Amsterdam, NL, vol. 66, No. 2-3, May 2000, pp. 159-175.
Opposition to EP 2034951 B1 in the Name of Merit Medical Systems, Inc. submitted Oct. 22, 2013.

(Continued)

*Primary Examiner* — Aradhana Sasan
(74) *Attorney, Agent, or Firm* — Sughrue Mion, PLLC

(57) ABSTRACT

A pharmaceutical product comprising lyophilized polymer matrix including a biologically active compound, of particular utility for embolization, having improved rehydration properties is packaged in an airtight package under vacuum.

32 Claims, 1 Drawing Sheet

(56) References Cited

OTHER PUBLICATIONS

Figure 1A:
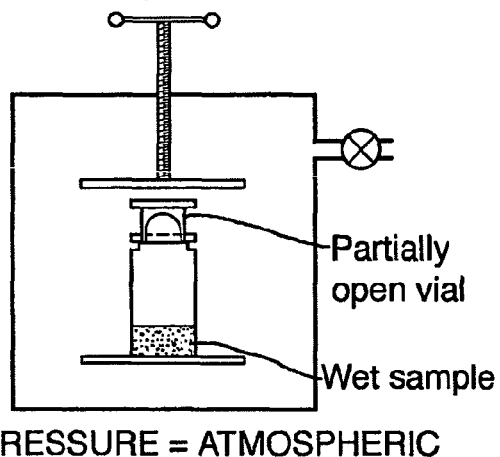

Patentee's Observations with amended Main Request, and 1st, 2nd, 3rd, and 4th Auxiliary Requests submitted Jun. 6, 2014 in EP Application No. 07786813.1.

Jean-Marc Malinovsky, MD, et al., "Motor and Blood Pressure Effects of Epidural Sustained-Release Bupivacaine from Polymer Microspheres: A Dose-Response Study in Rabbits", Anesth. Analg., vol. 81, 1995, pp. 519-524.

Guobao Wei, et al., "Nano-fibrous scaffold for controlled delivery of recombinant human PDGF-BB", Journal of Controlled Release, vol. 112, 2006, pp. 103-110.

A Guide to Freeze Drying for the Laboratory—An Industry Service Publication, Labconco Corporation, 2004, pp. 1-11.

Remington: The Science and Practice of Pharmacy, Lippincott Williams & Wilkins, A Wolters Kluwer Company, 21st Edition, 2005, pp. 828-831.

Product Information for Epsilon 1-6D Freeze Dryer obtained from website www.johnmorris.com; downloaded on Nov. 10, 2012.

Buckley Crist, "Time-Dependence of Pressure in Lyophilization Vials", PDA J. Pharm. Sci. And Tech., vol. 48, No. 4, 1994, pp. 189-196.

Vincent Wu and Buckley Crist, "An automated Method for Vacuum Testing Pharmaceutical Vials", PDA J. Pharm. Sci. and Tech., vol. 43, No. 4, 1989, pp. 179-182.

M. Chacón, et al., "Stability and freeze-drying of cyclosporine loaded poly($_{D,L}$ lactide-glycolide) carriers", European Journal of Pharmaceutical Sciences, vol. 8, 1999, pp. 99-107.

Wassim Abdelwahed, et al., "Freeze-drying of nanoparticles: Formulation, process and storage considerations", Advanced Drug Delivery Reviews, vol. 58, 2006, pp. 1688-1713.

Tanya P. Lin, et al., "Application of Frequency-Modulated Spectroscopy in Vacuum Seal Integrity Testing of Lyophilized Biological Products", PDA J. Pharm. Sci. and Tech., vol. 58, No. 2, 2004, pp. 106-115.

Physicians' Desk Reference, 58th Edition, published by Thomson PDR at Montvale, NJ, USA, 2004, pp. 1349-1353.

Antigoni Messaritaki, et al., "NMR and confocal microscopy studies of the mechanisms of burst drug release from PLGA microspheres", Journal of Controlled Release, vol. 108, 2005, pp. 271-281.

Stéphanie de Chasteigner, et al., "Freeze-Drying of Itraconazole-Loaded Nanosphere Suspensions: A Feasibility Study", Drug Development Research, vol. 38, 1996, pp. 116-124.

* cited by examiner

REHYDRATABLE PHARMACEUTICAL PRODUCT

The present invention relates to methods for formulating storage stable and easily rehydratable dried pharmaceutical compositions for administration to animals, especially for use as chemo-embolic compositions.

Embolisation therapy involves the introduction of an agent into the vasculature in order to bring about the deliberate blockage of a particular vessel. This type of therapy is particularly useful for blocking abnormal connections between arteries and veins, such as arteriovenous malformations (AVMs), and also for occluding vessels that feed certain hyper-vascularised tumours, in order to starve the abnormal tissue and bring about its necrosis and shrinkage. Examples of areas in which embolotherapy is increasingly being used are for the treatment of malignant hyper-vascular tumours such as hepatocellular carcinoma (HCC) and the treatment of uterine fibroids.

In the case of HCC it may be desirable to treat the tumour with an embolisation agent loaded with a chemotherapeutic agent. DC bead is an embolisation bead that can be loaded with doxorubicin prior to administration to a patient. It may be more convenient, however, if the beads could be supplied to the interventional radiologist with the doxorubicin already pre-loaded into the embolic agents. This saves time in preparation, handling of toxic drug and also the need to guess the amount of agent required for the procedure.

Due to the fact that many drugs, such as doxorubicin, are potentially unstable over time when in the hydrated form, an embolic adduct with pre-loaded drug may be lyophilised or freeze dried to remove excess water prior to terminal sterilization. The lyophilisation process results in the formation of a free flowing dry powder which is relatively stable during storage. This product is described in WO-A-04/071495.

In WO-4-04/071495 the polymer matrix is a cross-linked polyvinyl alcohol. Other particulate embolic materials are available, for instance based on alginates, albumin, gelatin, other synthetic polymers including PVA cross-linked with aldehydes, polyacrylates, polylactic- and polyglycolic acids. These may be in the form of irregular particles or, preferably, microspheres.

A number of other simple therapeutic compounds are being investigated in combination with microspheres for the embolization of other tumour types. Examples include irinotecan (WO-A-2006027567) and ibuprofen (WO-A-2006013376). In addition, newer drugs are becoming more complex in structure and there is a move away from simple molecular entities to much more complex entities which in some cases are of biological origin. These more complex molecular entities will probably be more unstable than corresponding simple molecular entities so the need for freeze drying of microspheres loaded with these species will probably be required to prolong their shelf-life.

One problem with freeze drying gels, eg hydrogels, or macroporous microspheres is that air pockets develop within the microspheres as the water is removed during the drying process. We have identified the fact that the presence of these air pockets is problematic when the dry beads are rehydrated. They can hinder the rate of hydration of the beads since the air needs to be exchanged with liquid for the bead to be fully hydrated. Since air is relatively hydrophobic and the aqueous liquids used for rehydration of the microspheres are hydrophilic, this process can be slow. In some cases, we have found hydration is totally inhibited by the presence of the air pockets within the microspheres. One other consequence of the presence of trapped air inside the microspheres is the buoyancy of the microspheres is altered. Since the air is less dense than the liquid for rehydration the beads tend to float. This can be very problematic and can affect the potential to obtain an adequate suspension of the beads when hydrated, in for instance, a mixture of water and contrast agent. In order to deliver the microspheres an adequate suspension is required in the hydration medium for sufficient time to allow ease of handling and effective delivery through a micro-catheter. Homogeneous delivery of microspheres and suspending/contrast medium allows control of the dose of microspheres and of active.

The present invention overcomes these problems of speed of hydration and ineffective suspension and avoids the addition of additional excipients to the particles.

According to the invention there is provided a new method for formulating the dried product suitable for direct administration into an animal after rehydration to form a suspension comprising:

i) a freezing step in which particles of polymer matrix swollen with water and having absorbed therein a non-volatile biologically active compound are cooled to a temperature below the freezing point of water;

ii) a lyophilisation step in which the cooled particles from step i) are subjected to a reduced pressure at which ice sublimes for a period during which at least a portion of the absorbed ice sublimes and water vapour is removed to form dried particles; and iii) a packaging step in which the dried particles are packaged;

characterised in that the packaging step is carried out under reduced pressure and the package containing the particles is substantially airtight and has an interior under vacuum.

The steps i) and ii) are generally carried out under the same conditions as in general lyophilisation processes for pharmaceuticals. It is convenient for further drying steps to be included, for instance between steps ii) and iii). Such further drying steps may be carried out to remove additional water and may be carried out at a temperature above the freezing point of water and at a reduced pressure, for instance at a pressure lower than the pressure for which step (i) is conducted. Suitable cycles are known comprising a combination of cold low pressure steps, followed by warmer, further reduced pressure steps, whereby water, including physically bound water, is removed from the polymer matrix.

Suitable pressures under which the lyophilisation step is carried out are in the range 0.01 mbar to 0.1 bar, preferably less than 100 mbar often less than 10 mbar, eg less than 1 mbar often 0.02 mbar and upwards. Suitable temperatures for the cooling and lyophilisation step are less than −10° C., preferably less than −15° C., often less than −20° C., for instance down to −50° C., preferably around −30° C.

Suitable pressures at which a further drying step between steps ii) and iii), are less than 0.2 mbar, preferably less than 0.1 bar, for instance down to 0.01 mbar, preferably about 0.05 mbar. Suitable temperatures are at least 0° C., preferably at least 25° C., more preferably at least 60° C.

Generally the temperatures and pressures are to be adapted dependant upon the volumes, especially the depths of the container of beads being treated. Shallow containers generally require less time to be frozen and shorter low pressure cycles than deep containers containing large quantities of materials. The freezing step may be carried out for a period of at least 5 minutes, for instance at least 10 minutes often an hour or more. The lyophilisation step may be carried out for a period of at least one hour, often overnight, for instance for a period of at least 8 hours or even more. The further drying step may be carried out over a period of at least an hour preferably two hours or more.

Although it is possible to carry out the method of the invention in bulk, with subsequent weighing and packaging in dosage forms, all carried out under vacuum, it is most convenient for steps i) and ii) or the method of the invention to be carried out with the swollen particles already contained within the vessels in which they are finally to be packaged. The vessels thus each contain a single dose of particles with biologically active compound. In such processes, the vessels are preferably formed of a rigid material, and have a mouth which is stoppered in the packaging step using a suitable airtight stopper. Suitable vessels are formed of glass, or may be rigid airtight plastics which are physically stable at the temperatures to which the material is subjected during the method of the invention. Most conveniently the method of the invention is carried out in an apparatus which is capable simultaneously of carrying out the freeze-drying and stoppering steps. Preferably substantially without allowing ingress air, oxygen or other gas after step ii) and before step iii). A suitable apparatus is commercially available under the trade name Epsilon 1-6D freeze drier by Christ and Genesis freeze drier by VirTis. Stoppers which are adequately airtight over useful storage periods are made of, for instance, butyl rubber although other low permeability rubbers which are stable at temperatures down to −30 or less ° C., may be used. It is particularly convenient for the stoppers to be formed of a material which may be pierced with a hyperdermic needle, so that rehydrating liquid may be easily injected into the stoppered vessels. During storage the pressure inside the vessel may increase as air slowly permeates through the stopper, but the permeability should be such that the pressure inside the vessel is less than atmospheric after storage periods of at least a month, preferably at least a year, for instance two years or more.

The method of the invention is particularly suitable for formulating compositions in which the polymer is a water-insoluble, preferably but not limited to a substantially non-biodegradable, pharmaceutically acceptable polymer. Since the starting material is water-swollen, then the polymer must be water-swellable. At the start of the method of the invention the polymer is preferably swollen substantially to equilibrium in aqueous liquid. Generally there is substantially no extra-particulate aqueous liquid, and the method may involve a preliminary step in which a suspension of swollen polymer particles in an aqueous liquid is subjected to an initial drying step in which extra-particulate liquid is removed, for instance by decantation, filtration or centrifugation.

The polymer is preferably crosslinked, most preferably covalently crosslinked, although ionically crosslinked polymers may also be usefully formulated using the method of the invention. Ionically crosslinked materials may comprise, for instance, ionically charged polymer, crosslinked with counterionically charged second polymer or, alternatively, with multivalent metal ions.

It may be suitable to use polymers which are derived from natural sources, such as albumin, alginate, gelatin, starch, chitosan or collagen, all of which have been used as embolic agents. Natural polymers or derivatives may be combined with synthetic polymers, by blending, inter molecular crosslinking or grafting. However, preferably the polymer is preferably substantially free of naturally occurring polymer or derivatives.

Preferably the polymer is based on a synthetic material, for instance formed by polymerisation of ethylenically unsaturated monomer, preferably in the presence of crosslinking monomer, for instance macromer or di- or higher-functional cross-linking monomers.

The ethylenically unsaturated monomers may include an ionic (including zwitterionic) monomer.

Copolymers of hydroxyethyl methacrylate, acrylic acid and cross-linking monomer, such as ethylene glycol dimethacrylate or methylene bisacrylamide, as used for etafilcon A based contact lenses may be used. Copolymers of N-acryloyl-2-amino-2-hydroxymethyl-propane-1,3-diol and N,N-bisacrylamide may also be used.

Other suitable polymers are cross-linked styrenic polymers e.g. with ionic substituents, of the type used as separation media or as ion exchange media, and polyphosphazenes.

Another type of polymer which may be used to form the water-swellable water-insoluble matrix is polyvinyl alcohol crosslinked using aldehyde type crosslinking agents such as glutaraldehyde. For such products, the polyvinyl alcohol (PVA) may be rendered ionic or may be substantially non-ionic. For instance the PVA may be rendered ionic by providing pendant ionic groups by reacting a functional ionic group containing compound with the hydroxyl groups. Examples of suitable functional groups for reaction with the hydroxyl groups are acylating agents, such as carboxylic acids or derivatives thereof, or other acidic groups which may form esters. Suitable commercially available embolic agents based on polyvinyl alcohol which may be used in the invention are Ivalon™, Trufill®, Contour SE™ and Hepasphere™.

The invention is of particular value where the polymer matrix is formed of a polyvinyl alcohol macromer, having more than one ethylenically unsaturated pendant group per molecule, by radical polymerisation of the ethylenic groups. Preferably the PVA macromer is copolymerised with ethylenically unsaturated monomers for instance including a non-ionic and/or ionic monomer.

The PVA macromer may be formed, for instance, by providing PVA polymer, of a suitable molecular weight such as in the range 1000 to 500,000 D, preferably 10,000 to 100,000 D, with terminal or mid-chain pendant vinylic or acrylic groups. Pendant acrylic groups may be provided, for instance, by reacting acrylic or methacrylic acid with PVA to form ester linkages through some of the hydroxyl groups. Other methods for attaching vinylic groups capable of polymerisation onto polyvinyl alcohol are described in, for instance, U.S. Pat. No. 4,978,713 and, preferably, U.S. Pat. Nos. 5,508,317 and 5,583,163. Thus the preferred macromer comprises a backbone of polyvinyl alcohol to which is linked, via a cyclic acetal linkage, an (alk)acrylaminoalkyl moiety. Example 1 of WO2004/071495 describes the synthesis of an example of such a macromer known by the approved named nelfilcon B which is useful in this invention. Preferably the PVA macromers have about 2 to 20 pendant ethylenic groups per molecule, for instance 5 to 10.

Where PVA macromers are copolymerised with ethylenically unsaturated monomers including an ionic monomer, the ionic monomer preferably has the general formula I $$Y^1BQ \qquad\qquad I$$

in which $Y^1$ is selected from

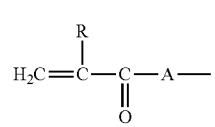
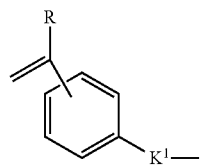

$CH_2=C(R)-CH_2-O-$, $CH_2=C(R)-CH_2OC(O)-$, $CH_2=C(R)OC(O)-$, $CH_2=C(R)-O-$, $CH_2=C(R)CH_2OC(O)N(R^1)-$, $R^2OOCCR=CRC(O)-O-$, $RCH=CHC(O)O-$, $RCH=C(COOR^2)CH_2-C(O)-O-$,

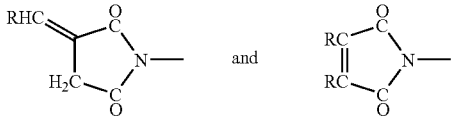

wherein:

R is hydrogen or a $C_1$-$C_4$ alkyl group;

$R^1$ is hydrogen or a $C_1$-$C_4$ alkyl group;

$R^2$ is hydrogen or a $C_{1-4}$ alkyl group or BQ where B and Q are as defined below;

A is $-O-$ or $-NR^1-$;

$K^1$ is a group $-(CH_2)_rOC(O)-$, $-(CH_2)_rC(O)O-$, $-(CH_2)_rOC(O)O-$, $-(CH_2)_rNR^3-$, $-(CH_2)_rNR^3C(O)-$, $-(CH_2)_rC(O)NR^3-$, $-(CH_2)_rNR^3C(O)O-$, $-(CH_2)_rOC(O)NR^3-$, $-(CH_2)_rNR^3C(O)NR^3-$ (in which the groups $R^3$ are the same or different), $-(CH_2)_rO-$, $-(CH_2)_rSO_3-$, or, optionally in combination with $B^1$, a valence bond and r is from 1 to 12 and $R^3$ is hydrogen or a $C_1$-$C_4$ alkyl group;

B is a straight or branched alkanediyl, oxaalkylene, alkanediyloxaalkanediyl, or alkanediyloligo(oxaalkanediyl) chain optionally containing one or more fluorine atoms up to and including perfluorinated chains or, if Q or $Y^1$ contains a terminal carbon atom bonded to B a valence bond; and Q is an ionic group.

An anionic group Q may be, for instance, a carboxylate, carbonate, sulphonate, sulphate, nitrate, phosphonate or phosphate group. The monomer may be polymerised as the free acid or in salt form. Preferably the $pK_a$ of the conjugate acid is less than 5.

A suitable cationic group Q is preferably a group $N^+R^4_3$, $P^+R^5_3$ or $S^+R^5_2$ in which the groups $R^4$ are the same or different and are each hydrogen, $C_{1-4}$-alkyl or aryl (preferably phenyl) or two of the groups $R^4$ together with the heteroatom to which they are attached from a saturated or unsaturated heterocyclic ring containing from 5 to 7 atoms the groups $R^5$ are each $OR^4$ or $R^4$. Preferably the cationic group is permanently cationic, that is each $R^4$ is other than hydrogen. Preferably a cationic group Q is $N^+R^4_3$ in which each $R^4$ is $C_{1-4}$-alkyl, preferably methyl.

A zwitterionic group Q may have an overall charge, for instance by having a divalent centre of anionic charge and monovalent centre of cationic charge or vice-versa or by having two centres of cationic charge and one centre of anionic charge or vice-versa. Preferably, however, the zwitterion has no overall charge and most preferably has a centre of monovalent cationic charge and a centre of monovalent anionic charge.

Examples of zwitterionic groups which may be used as Q in the present invention are disclosed in WO-A-0029481.

Where the ethylenically unsaturated monomer includes zwitterionic monomer, for instance, this may increase the hydrophilicity, lubricity, biocompatibility and/or haemocompatibility of the particles. Suitable zwitterionic monomers are described in our earlier publications WO-A-9207885, WO-A-9416748, WO-A-9416749 and WO-A-9520407. Preferably a zwitterionic monomer is 2-methacryloyloxy-2'-trimethylammonium ethyl phosphate inner salt (MPC).

In the monomer of general formula I preferably $Y^1$ is a group $CH_2=CRCOA-$ in which R is H or methyl, preferably methyl, and in which A is preferably NH. B is preferably an alkanediyl group of 1 to 12, preferably 2 to 6 carbon atoms. Such monomers are acrylic monomers.

There may be included in the ethylenically unsaturated monomer diluent monomer, for instance non-ionic monomer. Such a monomer may be useful to control the $pK_a$ of the acid groups, to control the hydrophilicity or hydrophobicity of the product, to provide hydrophobic regions in the polymer, or merely to act as inert diluent. Examples of non-ionic diluent monomer are, for instance, alkyl (alk) acrylates and (alk) acrylamides, especially such compounds having alkyl groups with 1 to 12 carbon atoms, hydroxy, and di-hydroxy-substituted alkyl(alk) acrylates and -(alk) acrylamides, vinyl lactams, styrene and other aromatic monomers.

In the polymer matrix, where there is ionic group present the level of ion is preferably in the range 0.1 to 10 meq $g^{-1}$, preferably at least 1.0 meq $g^{-1}$.

Where PVA macromer is copolymerised with other ethylenically unsaturated monomers, the weight ratio of PVA macromer to other monomer is preferably in the range of 50:1 to 1:5, more preferably in the range 20:1 to 1:2. In the ethylenically unsaturated monomer the ionic monomer is preferably present in an amount in the range 10 to 100 mole %, preferably at least 25 mole %.

The polymer may be formed into particles in several ways. For instance, the crosslinked polymer may be made as a bulk material, for instance in the form of a sheet or a block, and subsequently be comminuted to the desired size. Alternatively, the crosslinked polymer may be formed as such in particulate form, for instance by polymerising in droplets of monomer in a dispersed phase in a continuous immiscible carrier. Examples of suitable water-in-oil polymerisations to produce particles having the desired size, when swollen, are known. For instance U.S. Pat. No. 4,224,427 describes processes for forming uniform spherical beads (microspheres) of up to 5 mm in diameter, by dispersing water-soluble monomers into a continuous solvent phase, in a presence of suspending agents. Stabilisers and surfactants may be present to provide control over the size of the dispersed phase particles. After polymerisation, the crosslinked microspheres are recovered by known means, and washed and optionally sterilised. Preferably the particles eg microspheres, are swollen in an aqueous liquid, and classified according to their size.

The method of the invention is of particular utility where the rehydrated material is to be used as an embolic agent. The particles are preferably microspheres, that is are formed of substantially spherical or spheroidal particles. For embolic agents, such particles are generally separated into size fractions, whereby a surgeon may select microspheres of a size suited to embolise the vessels desired to be blocked in the method of treatment. For embolic materials, the particles generally have average diameter in the range 40 to 2000 µm, more preferably in the range 100 to 1500 µm. Preferably the particles have sizes such that they fall in a nominal range around 200 µm to 300 µm in width. Suitable size fractions have nominal sizes in the range 100 to 300, 300 to 500, 500 to 700, 700 to 900, 900 to 1200 µm. The particle sizes may be determined in the invention at various stages of the method. For instance the particle sizes may be determined on the swollen particles used as the starting materials for step i). Alternatively the particle sizes may be measured on the rehydrated products of the method of the invention.

Preferably the method of the invention comprises preliminary loading steps in which particles of non-loaded polymer are loaded with the biologically active compound. In such a method, the non-loaded polymer particles generally have sizes in the range defined above, when swollen to equilibrium at room temperature, in 0.9 wt % NaCl. The invention, as indicated above, is of particular value where the particles are to be rehydrated to form an aqueous suspension which is ultimately to be used as by direct administration to an animal, for instance by direct injection into a tumour or other target for local administration of the active. A preferred use is as embolic material. Of particular utility, embolic materials are utilised to embolise solid tumours, particularly malignant tumours although they may also be of use to embolise benign tumours such as uterine fibroids. Biologically active materials are preferably anti-tumour compounds, especially compounds which are unstable in the presence of water or other solvents. The invention is of particular value where the biologically active compound is an anti-neoplastic or often anti-proliferation, anti-migratory, immunosuppressant, analgesic, anti-inflammatory, anti-pyretic, anti-bacterial or anaesthetic agent.

The invention is of particular value for formulating anti-neoplastics and immunosuppressants, such as angiopeptin, and statins, such as sandostatin. Other suitable drugs include azacitidine, bleomycin and bleomycin sulphate, carboplatin, cisplatin, streptozoticin, capecitabine, vinorelbine, cyclosporin, cytabanine, decarbazine, anthracyclines such as daunorubicin, doxorubicin, epirubicin, mitoxantrone and banoxantrone. Other suitable chemotherapeutics include fluorouracil, gemcitabine, ifosfamide, methotrexate, mitomycin, mustine hydrochloride, lomustine, carmustine/BCNU, meclorethamine, vincristine, vinblastine, cytosar/cytarabine, peclitaxel, docetaxel, rapamycin and derivatives, such as tacrolimus, everolimus, biolimus, zotarolimus, and RAD001. Other suitable drugs include tyrphostin, tetradecylselenoacetic acid, tetradecylthioacetic acid, ethylisopropylamiloride, antithrombin, aggrastat, cilostazol, clexane, clopidogrel, dipyridamole, persantine, integrillin, abciximab, trapidil, VEGF, carredilol, estradiol and other estrogens, L-arginine, nitric oxide donors, probucol, quinaprilat, thioct-acid, telmisartan, zoledronate and matrix metalloproteinase inhibitors such as batimastat and marimastat.

Another class of compounds for which the invention is of utility include analgesics, anti-inflammatories, and anti-pyretics, such as Codeine sulphate, Diamorphine hydrochloride, fentanyl, hydromorphone hydrochloride, indomethacin, morphine hydrochloride and pethidine hydrochloride.

The invention may also be of utility for formulating anti-bacterials, for instance which may be administered into the arteriovenous system and/or may be administered in extended/controlled release formulations comprising polymer matrix formulations. Examples of such anti-bacterials are ampicillin, benzyl-penicillin, ceftazidime, ceftriaxone sodium, gemtamicin sulphate, tetracycline and vancomycin hydrochloride.

The method of loading the biologically active compound into the polymer matrix to form the starting material for step i) of the invention is selected according to the solubility of the active in solvents compatible with the polymer matrix and/or the swellability of the polymer in such solvents. For instance, in one preferred combination of components, the polymer is generally ionically charged, and is loaded by an ion-exchange type process with counterionically charged active compound. Where the active is doxorubicin hydrochloride, for instance, which is cationically charged, the polymer matrix is preferably anionically charged.

According to a preferred aspect of the invention the therapeutic active used in the present invention is an anthracycline compound, which comprises an anthraquinone group to which is attached an amine sugar. The amino group on the sugar is believed to associate with anionic groups in the polymer matrix, to allow high levels of loading and controlled delivery after administration. Alternatively the amine groups can be pendant groups on the anthracycline ring as for mitoxantrone and banoxantrone.

Examples of suitable anthracyclines have the general formula II

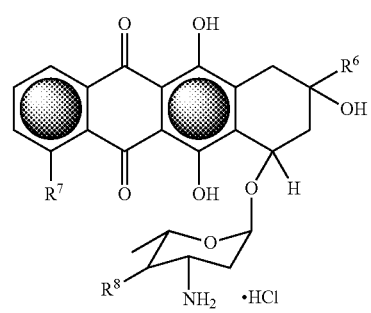

$R^6 = COCH_2OH\ R^7 = OCH_3\ R^8 = HO$ (axial) Doxorubicin
$R^8 = COCH_3\ R^7 = OCH_3\ R^8 = HO$ (axial) Daunorubicin
$R^6 = COCH_3\ R^7 = H\ R^8 = HO$ (axial) Idarubicin
$R^6 = COCH_2OH\ R^7 = OCH_3\ R^8 = HO$ (equatorial) Epriubicin Further a polymer matrix which allows good loading levels and release is an anionic poly(vinyl alcohol) based material, preferably formed by copolymerising the PVA macromer described above with an ionic monomer of the general formula I in which Q is an anionic group whose conjugate acid preferably has a pKa of 5 or less, We have found that doxorubicin, which has been thoroughly tested for efficacy on various tumours, has particularly interesting loading and release characteristics. The drug appears to have a particular affinity for poly(vinyl alcohol-graft-acrylamido propane sulphonic acid), so that high levels of doxorubicin are capable of incorporation into the polymer, and release over many days.

According to another preferred embodiment the pharmaceutical active is a camptothecin preferably a cationically charged camptothecin used in combination with an ionically charged polymer. Examples of such camptothecins have general formula has the general formula III

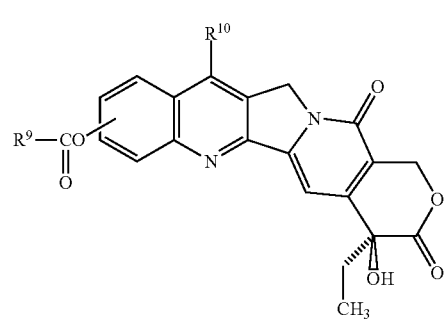

in which $R^{10}$ is H, lower $C_{(1-6)}$ alkyl, optionally substituted by a hydroxylamine, alkoxy, halogen, acyl or acyloxy group or halogen; and $R^9$ is chlorine or $NR^{11}R^{12}$ where $R^{11}$ and $R^{12}$ are the same or different and each represents a hydrogen atom, a substituted or unsubstituted $C_{1-4}$ alkyl group or a substituted or unsubstituted carbocyclic or heterocyclic group, or $R^{11}$ and $R^{12}$ together with the nitrogen atom to which they are attached form an optionally substituted heterocyclic ring which may be interrupted by —O—, —S— or >NR$^{13}$ in which R$^{13}$ is a hydrogen atom, a substituted or unsubstituted C$_{1-4}$ alkyl group or a substituted or unsubstituted phenyl group;

and wherein the grouping —O—CO—R$^9$ is a bonded to a carbon atom located in any of the 9, 10 or 11 positions in the A ring of the camptothecin compound, including salts thereof.

Preferably R$^9$ is NR$^{11}$R$^{12}$ in which R$^{11}$ and R$^{12}$ together with the nitrogen atom from an optionally substituted heterocyclic ring. Most preferably R$^9$ is

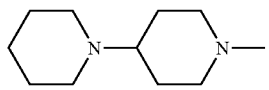

Preferably R$^9$ is substituted at the 10 position in the camptothecin. Preferably R$^{10}$ is ethyl.

The therapeutic active may be incorporated into the polymer matrix by a variety of techniques. In one method, the therapeutic active may be mixed with a precursor of the polymer, for instance a monomer or macromer mixture or a cross-linkable polymer and cross-linker mixture, prior to polymerising or crosslinking. Alternatively, the active may be loaded into the polymer after it has been crosslinked. For instance, particulate dried polymer may be swollen in a solution of therapeutic active, preferably in water, optionally with subsequent removal of non-absorbed agent and/or evaporation of solvent. A solution of the active, in an organic solvent such as an alcohol, or, more preferably, in water, may be sprayed onto a moving bed of particles, whereby drug is absorbed into the body of the particles with simultaneous solvent removal. Most conveniently, we have found that it is possible merely to contact swollen particles suspended in a continuous liquid vehicle, such as water, with a solution of drug, over an extended period, whereby drug becomes absorbed into the body of the particles. This is believed to be analogous to a cation exchange type process. The swelling vehicle may subsequently be removed or, conveniently, may be retained with the particles as part of the product for subsequent use as an embolic agent.

The drug loaded particles are then recovered from excess loading solution or solvent and subjected to the above described drying and packaging process.

The present invention comprises further a method preparing a pharmaceutically acceptable suspension for administration to an animal in which the product of the method of the invention defined above is rehydrated by adding to the package of dried product a pharmaceutically acceptable sterile aqueous liquid and, optionally, a contrast medium, to form a suspension of swollen particles in a continuous aqueous liquid.

The pharmaceutically acceptable sterile aqueous liquid is, for instance, physiological saline, deionised water or, preferably, phosphate buffered saline. Preferably the sterile aqueous liquid is added directly into the airtight package by puncturing this with a hypodermic needle through which the liquid is directed without allowing ingress of gases, such as air or oxygen. Once the aqueous rehydrating liquid and particles have formed a stable suspension, this is preferably combined with contrast medium and mixed, to form a suspension ready for administration to a patient.

There is also provided in the invention a method of treatment of an animal in which the suspension formed in the preceding paragraph is administered to an animal, preferably by administration into an artery to embolise blood vessels, preferably to embolise a solid tumour.

According to the invention there is also provided a new airtight package containing, under vacuum, lyophilised particles of water-swellable water-insoluble biocompatible polymer into which is absorbed a pharmaceutically acceptable biologically active compound, in which the particles are swellable in 0.9 wt % saline at room temperature to sizes in the range 40 to 2000 μm.

In this aspect of the invention the polymer and biologically active compound have the preferred properties defined above in connection with the first aspect of the invention.

Figure 1B:
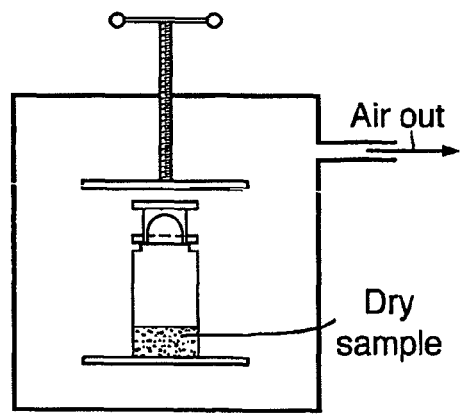
Figure 1C:
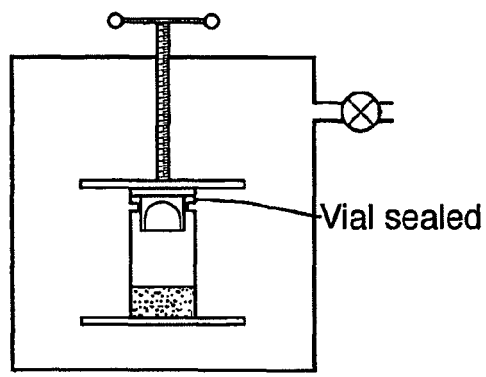
Figure 1D:
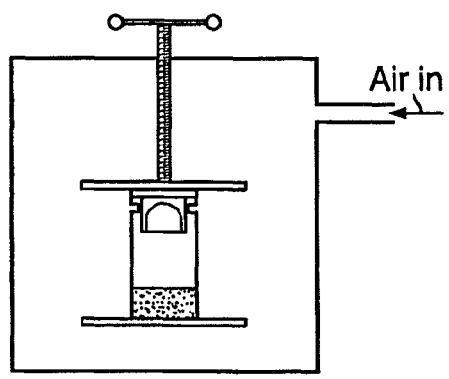
Figure 1E:
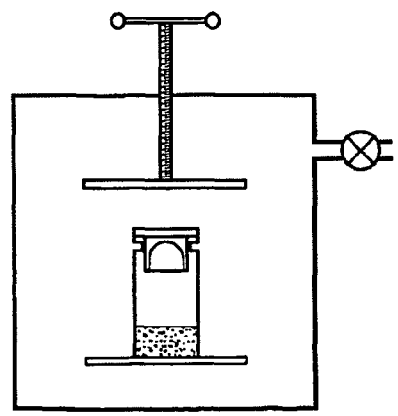

FIG. 1 is a diagrammatic representation of the apparatus in which the examples are carried out showing how the vials are stopped without allowing ingress of air.

The invention is illustrated further in the accompanying examples.

EXAMPLE 1

Microsphere Production

The spheres are synthesised by a method of suspension polymerisation in which an aqueous phase comprising a solution (about 700 g) containing a PVA macromer, nelfilicon A, (around 80 g), 2-acrylamido-2-methyl propane sulphonate sodium salt (70 g) and potassium persulphate initiator (around 5 g) is suspended in an organic phase of butyl acetate (3l) and 5 g cellulose acetate butyrate (solution in ethyl acetate) in a stirred reactor. By employing rapid mixing the aqueous phase can be dispersed to form droplets, the size and stability of which can be controlled by factors such as stirring rates, viscosity, ratio of aqueous/organic phase. Polymerisation of the dispersed monomer/macromer solution is initiated by the addition of TMEDA and raising the temperature to over 50° C. for several hours under nitrogen. After cooling to room temperature the product is purified by removing the butyl acetate by filtration followed by washing steps with solvents, vacuum dried to remove solvents then the microspheres are equilibrated at 60° C. in water to fully re-hydrate. The spheres are sieved using a 316L stainless steel vortisieve unit (MM Industries, Salem Ohio) with stainless steel sieving trays with mesh sizes ranging from 32 to 1200 μm including sizes about 100 μm, 300 μm, 500 μm, 700 μm and 900 μm. Spheres collected in the 32 μm sieve are discarded.

Drug Loading

For each size of microsphere used, 0.5 ml was transferred in to 2, 1 ml syringes, one for drug take up and the second to act as a control. The sizes chosen for the experiment were, 100-300 μm, 300-500 μm, 500-700 μm and 850-1000 μm. Additionally a further 3 syringes of the 500-700 μm were prepared in order to validate the procedure. 11, 10 ml glass vials were covered in foil, to prevent degradation of the doxorubicin by light for the duration of the experiment. A standard curve was created. Using the 80 ml, 20 mg/ml drug solution, the following concentrations were prepared and their absorbances (at 483 nm) measured: 100 μg/ml, 50 μg/ml, 25 μg/ml, 12.5 μg/ml, 6.25 μg/ml and 3.125 μg/ml. The resulting absorbances were plotted on a graph and the equation of the line used to calculate the concentration of drug that was up-taken by the beads in the experiment. Four of the vials were filled with 5 ml of distilled water (ROMIL) to be used as controls when the beads were added. To the remaining 7 vials were added 5 ml of the drug solution at the desired concentration. The starting absorbance and therefore concentration of the solution was already known from the preparation of the standard curve. (In order to measure the absorbance of the 20 mg/ml solution it was necessary to dilute it 200 times, using the concentration 100 µg/ml. This 1:200 dilution was carried through for the duration of measuring the uptake of the solution by the beads.) The stopwatch was started as soon as the first set of microspheres were added to the first drug containing vial, microspheres were added to each of the remaining 6 vials working from smallest to largest. Once sealed using the caps they were placed on the rotary mixer. The process was repeated for the control samples. The absorbances were measured in the same order as the vials were set up at time intervals of 0.167 hr (10 min), 0.5 hr, 1 hr, 2 hr, 24 hr and 96 hr. From the data the amount of drug (in mg) per 1 ml of microspheres and the % uptake of drug by 1 ml of microspheres could be calculated.

Epsilon 1-6D freeze dryer is used in the next step of the production of 100-300, 300-500, 500-700 and 700-900 µm (1.5±0.1 ml) preloaded with 37.5 mg doxorubicin per vial. The vials are type 1 tubular neutral glass 10 ml vials and the bungs are butyl rubber igloo lyophilisation stoppers. The lyophilisation program has been designed to operate when fully loaded with 345 vials of microspheres.

Epsilon 1-6D freeze dryer with Lyo Screen Control (LSC) panel and Pfeiffer DUO 10 Rotary Vane Vacuum pump. The apparatus is controlled by Lyolog LL-1 documentation software.

The Epsilon 1-6D is a pilot scale freeze dryer. The system consists of a chamber with three liquid controlled cooled/heated shelves with a temperature range of −40 to 80° C. on which samples are frozen. The ice condenser, whose minimum temperature is −60° C., is located in an adjacent chamber separated by an intermediate valve. The shelves and ice condenser are cooled using two cooling machines. The chamber pressure is achieved using a Pfeiffer DUO 10 rotary vane vacuum pump.

The Epsilon 1-6D can lyophilise a maximum of 345 vials (10 ml) per cycle, i.e. with 115 vials per shelf.

The microspheres are lyophilised by freezing at about −30° C. without a vacuum, at least 1 h, then reducing the pressure gradually over a period of about half an hour to a pressure of in the range 0.35-0.40 mbar, while allowing the temperature to rise to about −20° C. and holding the conditions at this temperature and pressure overnight, followed by raising the temperature to room temperature for a period of about 1-2 hours at the same time pressure, followed by a period at room temperature with the pressure reduced to about 0.05 mbar, to a total cycle time of 24 hours.

At the end of the cycle and substantially without allowing ingress of air the vials are stoppered under vacuum by turning the vial closing mechanism that lowers the shelves to stopper the vials on the shelf beneath. The chamber is then aerated to allow the chamber to reach atmospheric pressure. The shelves are then returned to their original position and the chamber opened.

As a control, the process is repeated but the chamber is allowed to equilibrate to atmospheric pressure by allowing ingress of air to atmospheric pressure prior to the vials being stoppered.

The products of the method of the invention loaded with doxorubicin (typically 25 to 40 mg drug per ml bead) and of the comparison method are then rehydrated by injection of 3 ml of water and 3 ml contrast agent (e.g. Lipiodiol) using a conventional hypodermic needle attached to a syringe to pierce the stopper. The vials are shaken for 3 minutes manually or using a mechanical shaken. The method of the invention thus allows faster rehydration and easier handling both of which enable more control of dosage which are all of high importance for a surgeon wishing to immediately administer the suspension to a patient undergoing surgery. Even after longer periods of shaking, the control microspheres include a fraction which float on the surface.

The method of the invention thus allows easier handling, improved dosage control, and faster rehydration, all of high importance for a surgeon or interventional radiologist wishing to immediately administer the suspension to a patient undergoing surgery.

EXAMPLE 2

The beads produced as in Example 1 are loaded with irinotecan loaded at a level of around 50 mg drug per ml beads. The lyophilisation cycle was the same as that used in example 1. The beads could easily be rehydrated upon addition of saline to the container under lower than atmospheric pressure, the beads quickly sinking and being capable of forming a homogeneous suspension.

EXAMPLE 3

Alginate microspheres are formed as follows. An aqueous solution of high G alginate (recovered as described in WO-A-00/09566) is crosslinked by spraying droplets of the 2% solution into a precipitation bath comprising a solution of calcium ions, followed by collection of the formed microspheres. The microspheres have an average size of 215 µm (standard deviations 3 µm). After cleaning, 0.2 ml of 2% alginate microsphere suspension is transferred into a vial. Excess liquid is decanted, then 1.39 mls of 10.07 mg per ml aqueous doxorubicin solution is added to the microspheres. The mixture is shaken overnight. After this time, the loading capacity is determined by measuring the concentration of a portion of decanted excess loading solution. This reveals a loading capacity of around 50 to 60 mg doxorubicin per ml of bead suspension. Excess loading solution is removed and the bead slurry subjected to freeze drying in the vial.

The freeze drying cycle is substantially as described in example 1. At the end of the cycle the vials are stoppered under the final vacuum.

When resuspended in 0.9 wt % saline, the beads rehydrated rapidly, and sank in the suspension.

The invention claimed is:
1. A method of preparing a pharmaceutical suspension for administration to an animal comprising the steps:
   i) providing particles of polymer matrix swollen with water and having absorbed therein a non-volatile biologically active compound wherein the polymer is a water-insoluble water-swellable pharmaceutically acceptable polymer;
   ii) cooling the swollen particles from step i) in a freezing step to a temperature below the freezing point for water whereby the water in the polymer matrix forms absorbed ice;
   iii) in a lyophilisation step subjecting the cooled particles from step ii) to a reduced pressure at which ice sublimes for a period during which at least a portion of the absorbed ice sublimes and water vapour is removed;
   iv) in a packaging step, packaging the dried particles under reduced pressure and into a package that is substantially airtight and has an interior under vacuum to form packaged particles;
   v) storing the package for optionally a storage period of 1 day to 10 years; and
   vi) rehydrating the dried particles by adding to the package of dried product a pharmaceutically acceptable sterile aqueous liquid, without allowing ingress of air, and, optionally, a contrast medium, to form a suspension of swollen particles in the aqueous liquid, wherein said swollen particles in the suspension in the aqueous liquid have particle sizes in the range 40 to 2000 µm.

2. A method of treatment of an animal in which there is prepared a pharmaceutical suspension for administration to an animal in which the product of a method according to claim 1, optionally after a storage period of 1 day to 10 years, is rehydrated by adding to the package of dried product a pharmaceutically acceptable sterile aqueous liquid, substantially without allowing ingress of air, and, optionally, a contrast medium, to form a suspension of swollen particles in the aqueous liquid and the suspension is administered to an animal.

3. An airtight package containing, under vacuum, lyophilised particles of water-swellable water-insoluble biocompatible polymer into which is absorbed a pharmaceutically acceptable biologically active compound, in which the particles are swellable in 0.9 wt % saline at room temperature to sizes in the range 40 to 2000 µm.

4. Package according to claim 3 in which the package is rigid.

5. Package according to claim 4 in which the package is of glass closed with an airtight closure, including a stopper penetrable by hypodermic needle.

6. Package according to claim 3, in which the polymer is a water-insoluble, pharmaceutically acceptable polymer.

7. Package according to claim 6, in which the polymer is cross-linked.

8. Package according to claim 6, in which the polymer is based on poly(vinyl alcohol).

9. Packing according to claim 6, in which the polymer is formed by polymerisation of ethylenically unsaturated monomers.

10. Package according to claim 3, in which the particle sizes are selected such that upon rehydration in 0.9 wt % saline at room temperature, the average particle size is in the range 40 to 2000 µm.

11. Package according to claim 3, in which the particles are substantially spherical in shape.

12. Package according to claim 3, in which the biologically active compound is selected from anti-proliferatives, including anti-neoplastics, and anti-migratories, immunosuppressants, analgesics, anti-inflammatories, anti-pyretics, anaesthetic and anti-bacterials.

13. Package according to claim 12 in which the biologically active compound is an anti-neoplastic agent selected from angiopeptin, statins, such as sandostatin, azacitidine, bleomycin and bleomycin sulphate, carboplatin, cisplatin, streptozoticin, capecitabine vinorelbine, cyclosporin, cytabanine, dacarbazine, anthracyclines such as daunorubicin hydrochloride and doxorubicin hydrochloride, fluorouracil, halopiridol, gemcitabine, ifosfamide, methotrexate, mitoxantrone, banoxantrone, mitomycin, mustine hydrochloride, lomustine, carmustine/BCNU, meclorethamine, vincristine, vinblastine and cytosar/cytarabine, paclitaxel, docetaxel, rapamycin and derivatives, such as tyrphostin, tacrolimus, everolimus, biolimus, zotarolimus and RAD001, tetradecylselenoacetic acid, tetradecyl thioacetic acid, ethylisopropylamiloride, antithrombin, aggrastat, cilostazol, clexane, clopidogrel, dipyridamole, persantine, integrillin, abciximab, trapidil, matrix metalloproteinase inhibitors such as batimastat and marimastat, VEGF, carvedilol, estradiol and other estrogens, L-arginine, nitric oxide donors, probucol, quinaprilat, thioctacid, telmisartan, zoledronate and irinotecan.

14. A method according to claim 1, in which the ethylenically unsaturated monomers include macromer comprising a backbone of polyvinyl alcohol to which is linked, via a cyclic acetal linkage, to a (alk)acrylaminoalkyl moiety.

15. A method according to claim 2, in which the suspension is administered into an artery to embolise blood vessels.

16. A method according to claim 1, in which the biologically active compound is a statin.

17. A method according to claim 16, in which the statin is sandostatin.

18. A method according to claim 1, in which the biologically active compound is a rapamycin derivative.

19. A method according to claim 18, in which the rapamycin derivative is selected from the group consisting of tyrphostin, tacrolimus, everolimus, biolimus and zotarolimus.

20. A method according to claim 1, in which the biologically active compound is a matrix metalloproteinase inhibitor.

21. A method according to claim 20, in which the matrix metalloproteinase inhibitor is selected from the group consisting of batimastat and marimastat.

22. A method according to claim 1 wherein the polymer is cross-linked.

23. A method according to claim 1 wherein the polymer is based on poly(vinyl alcohol).

24. A method according to claim 1 in which the polymer is formed by polymerisation of ethylenically unsaturated monomers.

25. A method according to claim 1 in which the particles are substantially spherical in shape.

26. A method according to claim 1 wherein the biologically active compound is an anthracycline.

27. A method according to claim 26 in which the anthracycline is selected from the group consisting of daunorubicin hydrochloride and doxorubicin hydrochloride.

28. A method according to claim 1, in which the package comprises a vessel which is substantially rigid and has a mouth closed by a stopper and in which the pressure inside the package is less than 0.95 bar.

29. A method according to claim 1, in which the temperature to which the particles are cooled in the cooling step is less than −20° C.

30. A method according to claim 1, in which the lyophilisation step is carried out at a temperature less than −20° C.

31. A method according to claim 1, in which the pressure in the lyophilisation step is reduced to less than 100 mbar.

32. A method according to claim 1, in which the biologically active compound is selected from anti-proliferatives, including anti-neoplastics, and anti-migratories, immunosuppressants, analgesics, anti-inflammatories, anti-pyretics, anaesthetic and anti-bacterials.

* * * * *